United States Patent
Robert

(10) Patent No.: US 9,808,547 B2
(45) Date of Patent: Nov. 7, 2017

(54) SANITIZER

(71) Applicant: AMERICAN DRYER, INC., Livonia, MI (US)

(72) Inventor: Michael E. Robert, Farmington Hills, MI (US)

(73) Assignee: DM TEC, LLC, Livonia, MI (US)

( * ) Notice: Subject to any disclaimer, the term of this patent is extended or adjusted under 35 U.S.C. 154(b) by 0 days.

(21) Appl. No.: 14/785,262

(22) PCT Filed: Apr. 16, 2014

(86) PCT No.: PCT/US2014/034282
§ 371 (c)(1),
(2) Date: Oct. 16, 2015

(87) PCT Pub. No.: WO2014/172410
PCT Pub. Date: Oct. 23, 2014

(65) Prior Publication Data
US 2016/0067363 A1   Mar. 10, 2016

Related U.S. Application Data

(60) Provisional application No. 61/813,399, filed on Apr. 18, 2013.

(51) Int. Cl.
*A61L 2/14* (2006.01)
*H01J 37/30* (2006.01)
(Continued)

(52) U.S. Cl.
CPC ............... *A61L 2/14* (2013.01); *A61L 2/20* (2013.01); *H01J 37/3002* (2013.01); *H01T 23/00* (2013.01); *A61L 2202/11* (2013.01)

(58) Field of Classification Search
CPC ........ A61L 2/00; A61L 2/0029; A61L 2/0047; A61L 2/08; A61L 2/10; A61L 9/00; A61L 9/18; A61L 9/20
(Continued)

(56) References Cited

U.S. PATENT DOCUMENTS 2,392,808 A   1/1946   Chapman
2,928,941 A   3/1960   Hicks et al.
(Continued)

FOREIGN PATENT DOCUMENTS

CN   2169935   6/1994
CN   2235509   9/1996
(Continued)

OTHER PUBLICATIONS

Gadri, Ben et al.; Sterilization and plasma processing of room temperature surfaces with a one atmosphere uniform glow discharge plasma (OAUGDP); Surface & Coatings Technology; vol. 131, pp. 528-542 (2000).
(Continued)

*Primary Examiner* — Nicole Ippolito
(74) *Attorney, Agent, or Firm* — Craig A. Phillips; Dickinson Wright PLLC

(57) ABSTRACT

A sanitizer for sanitizing various surfaces including hands, hardware, fixtures, appliances, countertops, equipment, utensils and more and more specifically to a chemical-free sanitizer, more specifically to an ozone-free sanitizer and yet more specifically to an electronic sanitizer and yet more specifically to an ion source sanitizer.

12 Claims, 11 Drawing Sheets

(51) Int. Cl.
*A61L 2/20* (2006.01)
*H01T 23/00* (2006.01)

(58) Field of Classification Search
USPC .......................... 250/453.11, 454.11, 455.11
See application file for complete search history.

(56) References Cited

U.S. PATENT DOCUMENTS

| | | | |
|---|---|---|---|
| 3,443,155 | A | 5/1969 | Schweriner |
| 3,584,766 | A | 6/1971 | Hart |
| 3,609,446 | A | 9/1971 | Hursh et al. |
| 3,697,806 | A | 10/1972 | Herbert, Jr. |
| 3,816,793 | A | 6/1974 | Radloff et al. |
| 3,828,239 | A | 8/1974 | Nagai et al. |
| 3,840,797 | A | 10/1974 | Aggen et al. |
| 3,866,086 | A | 2/1975 | Miyoshi et al. |
| 3,878,469 | A | 4/1975 | Bolasny |
| 3,943,407 | A | 3/1976 | Bolasny |
| 3,981,695 | A | 9/1976 | Fuchs |
| 4,069,665 | A | 1/1978 | Bolasny |
| 4,282,460 | A | 8/1981 | Luz et al. |
| 4,292,592 | A | 9/1981 | Birdwell et al. |
| 4,301,497 | A | 11/1981 | Johari |
| 4,597,781 | A | 7/1986 | Spector |
| 4,616,300 | A | 10/1986 | Santelmann, Jr. |
| 4,689,715 | A | 8/1987 | Halleck |
| 4,789,801 | A | 12/1988 | Lee |
| 4,893,227 | A | 1/1990 | Gallios et al. |
| 4,974,115 | A | 11/1990 | Breidegam et al. |
| 5,010,869 | A | 4/1991 | Lee |
| 5,055,963 | A | 10/1991 | Partridge |
| 5,317,155 | A | 5/1994 | King |
| 5,452,720 | A | 9/1995 | Smith et al. |
| 5,484,472 | A | 1/1996 | Weinberg |
| 5,930,105 | A | 7/1999 | Pitel et al. |
| 6,201,359 | B1 | 3/2001 | Raets |
| 6,771,519 | B2 | 8/2004 | Frus et al. |
| 7,218,500 | B2 | 5/2007 | Adachi |
| 7,564,671 | B2 | 7/2009 | Kato et al. |
| 7,601,970 | B2 | 10/2009 | Lee |
| 7,649,728 | B2 | 1/2010 | Fujita et al. |
| 7,662,348 | B2 | 2/2010 | Taylor et al. |
| 7,854,900 | B2 | 12/2010 | Takeda et al. |
| 7,920,368 | B2 | 4/2011 | Fujiwara et al. |
| 7,995,321 | B2 | 8/2011 | Shimada |
| 8,009,405 | B2 | 8/2011 | Gefter et al. |
| 8,149,371 | B2 | 4/2012 | Oohira |
| 8,605,407 | B2 | 12/2013 | Gefter et al. |
| 8,773,837 | B2 | 7/2014 | Partridge et al. |
| 8,885,317 | B2 | 11/2014 | Partridge |
| 2002/0014410 | A1 | 2/2002 | Silveri et al. |
| 2004/0184975 | A1 | 9/2004 | Anno |
| 2005/0028254 | A1 | 2/2005 | Whiting |
| 2005/0205080 | A1* | 9/2005 | Kuroda ................ F23N 5/102 126/116 A |
| 2006/0018811 | A1 | 1/2006 | Taylor et al. |
| 2006/0243762 | A1 | 11/2006 | Sassoon |
| 2007/0279829 | A1 | 12/2007 | Gefter et al. |
| 2008/0250928 | A1 | 10/2008 | Desalvo et al. |
| 2009/0316445 | A1 | 12/2009 | Mowrer et al. |
| 2010/0064545 | A1 | 3/2010 | Pollack et al. |
| 2010/0065535 | A1 | 3/2010 | Zheng et al. |
| 2010/0157503 | A1 | 6/2010 | Saito et al. |
| 2011/0102963 | A1 | 5/2011 | Sekoguchi |
| 2011/0133098 | A1 | 6/2011 | Kitagaito et al. |
| 2011/0150710 | A1 | 6/2011 | Tsuda et al. |
| 2012/0081929 | A1 | 4/2012 | Dvorsky |
| 2012/0200982 | A1 | 8/2012 | Partridge |
| 2012/0224293 | A1 | 9/2012 | Partridge et al. |
| 2012/0240968 | A1 | 9/2012 | Schumacher |
| 2012/0314333 | A1 | 12/2012 | Takeda et al. |
| 2013/0095000 | A1 | 4/2013 | Yamamoto et al. |
| 2013/0201730 | A1 | 8/2013 | Luo |
| 2013/0232807 | A1 | 9/2013 | Robert et al. |
| 2014/0285084 | A1 | 9/2014 | Fomani et al. |
| 2015/0037201 | A1* | 2/2015 | Armour ................ A61B 19/38 422/3 |
| 2016/0104595 | A1 | 4/2016 | Nishida et al. |

FOREIGN PATENT DOCUMENTS

| | | |
|---|---|---|
| CN | 1536281 | 10/2004 |
| CN | 201311011 | 9/2009 |
| CN | 203423631 | 2/2014 |
| CN | 203481626 | 3/2014 |
| EP | 0368858 | 5/1995 |
| EP | 1637811 | 3/2006 |
| EP | 1625890 | 6/2011 |
| JP | 2001043992 | 2/2001 |
| JP | 2002216994 | 8/2002 |
| JP | 5185250 | 4/2013 |
| WO | 2010144528 | 12/2010 |
| WO | 2013119283 | 8/2013 |

OTHER PUBLICATIONS

Prutchi et al., "d.i.y. 250 kV High Voltage DC Power Supply with Neat Trick for Switching Polarity," http://www.diyphysics.com/2012/02/09/d-i-y-250-kv-high-voltage-dc-power-supply-with-neat-trick-for-switching-polarity/ (accessed May 8, 2015).

"Flyback Transformer," Wikipedia, http://en.wikipedia.org/wiki/Flyback_transformer (accessed May 8, 2015).

"Basic Single-Output Flyback Converter Circuit Diagram," http://datasheetoo.com (accessed May 15, 2014).

Schmidt et al., "Microfabricated differential mobility spectrometry with pyrolysis gas chromatography for chemical characterization of bacteria," Anal Chem. 2004, Abstract.

International Search Report, dated Jun. 25, 2015 (PCT/US2015/020288).

* cited by examiner

SANITIZER

CROSS-REFERENCE TO PRIOR APPLICATIONS

This U.S. National Stage Patent Application claims the benefit of PCT International Patent Application Serial No. PCT/US2014/034282 filed Apr. 16, 2014 entitled "Sanitizer," which claims the benefit of U.S. Provisional Patent Application Ser. No. 61/813,399 filed Apr. 18, 2013, entitled "Sanitizer," the entire disclosures of the applications being considered part of the disclosure of this application and hereby incorporated by reference.

BACKGROUND OF THE INVENTION

1. Field of the Invention

The present invention is directed to a sanitizer for sanitizing various surfaces including hands, hardware, fixtures, appliances, countertops, equipment, utensils and specifically to a chemical-free sanitizer, more specifically to an ozone-free sanitizer and yet more specifically to an electronic sanitizer and yet more specifically to an ion source sanitizer.

2. Description of the Prior Art

It is well known that many infectious diseases and pathogens are communicated through touch or contact. Therefore, commonly touched items in public areas and facilities such as doorknobs, handles, fixtures, and other surfaces may spread such infectious diseases and pathogens. People are particularly concerned with touching various surfaces in public restrooms even communal restrooms at a work place due to actual or perceived sanitary conditions of those restrooms and the users of the restrooms. However, contact with door handles, knobs and other fixtures related to the restroom is many times unavoidable. Other exemplary surfaces that may be unavoidable and be contaminated with pathogens from people or other sources, including food preparation, may include drinking fountains, kitchen counter tops, shared appliances, and nearly any other surface that multiple people may contact. Therefore, many people generally find it desirable to avoid or minimize contact with such surfaces when possible.

People are particularly concerned with the cleanliness of surfaces after washing their hands or before the eating of food. However, touching many of the surfaces in a restroom after washing hands or in a kitchen while preparing food, particularly in a work place kitchen is unavoidable. For example, in most restrooms as a person must touch the handle of the door to exit a restroom, touch the same faucet handle to turn off the water that was used, to turn on the water, and other potentially contaminated surfaces, it is easy to recontaminate the recently cleaned hands. In a kitchen, other than door and fixture handles such as faucets, a refrigerator door handle, the surface of a microwave and other appliances, and light and appliance switches and controls may all be contaminated with various pathogens. Some people use extra paper towels to cover and touch handles of door or faucets in certain situations; however, generally this is wasteful and adds expense for the facility, including increased paper cost as well as increased labor cost for replacing the paper products more frequently.

A number of prior methods have been proposed, all having limited success or significant drawbacks in sanitizing various surfaces including the door handles. The first method is generally a more frequent cleaning of such surfaces; however, this increases labor costs and generally people are distrustful that the surfaces have been properly cleaned and with enough frequency. In addition, even if the cleaning was thorough and no pathogens exist on the surface, the very first contact by a person may place undesirable infectious agents or pathogens on the surface and any subsequent users may come in contact with such infectious agents or pathogens. Therefore, the more frequent cleanings do not solve the problem of contaminated surfaces.

Some facilities provide various cleaning wipes, liquids, or sponges that may be used for cleaning of the surface by a user. While these are generally capable of cleaning the surface, the use is limited to a person actually using them. A big disadvantage to these wipes, liquids, or sponges is that they require frequent replacement thereby increasing the cost for the facility. Many times these anti-bacterial sprays, liquids or wipes are empty creating an undesirable situation for the person using the facility.

To address the above problems, some manufacturers have introduced various electronic chemical sanitizers that at regular intervals with little to no interaction with a user or upon activation of a sensor, sprays a liquid on the desired surface. In addition to the increased maintenance cost as well as product cost of replacing the battery and the chemical or wet material of these chemical sanitizers, most people find it undesirable to touch a moist or damp surface, such as a moist or damp door handle even if the moisture or liquid is a sanitizing chemical. In addition, many people do not like the smell or have various chemical allergies to the chemical being used on the door handle, making widespread use undesirable. More specifically, such as in an office setting, if one worker has a chemical allergy to the cleaning device that is being used, which on a timed or activated interval sprays a door handle, it may prevent further use in that facility. To address the above problems, some people have proposed using ultraviolet sanitizers that when positioned or placed over a non-porous surface effectively sterilizes and sanitizes the surface. While such devices prevent the spread of pathogens passed on by contact by direct exposure to ultraviolet light, these devices generally are power intensive and require frequent battery changes or recharging, unless they are hardwired into a facility's electrical system and if not properly positioned or configured may have adverse health effects. Therefore, to sanitize the hardware of doors, which do not typically have readily available power supplies, even where the use is controlled by a preprogrammed timer or motion sensing to limit battery drain, the useful life is still relatively limited, requiring regular maintenance by the facility to recharge or replace batteries thereby raising costs. Many people are also concerned regarding sticking their hands on a door handle to open it where it may be bathed in ultraviolet light. The positioning of many of these devices is above a door handle or counter top which places it high enough that smaller people, such as children, may inadvertently look directly at the ultraviolet lamp which is undesirable and could cause vision issues. Therefore, the implementation of these devices as sanitizers for various fixtures that cannot fit in an enclosure has been limited due to their serious drawbacks.

To address the shortcomings with various chemical and ultraviolet light sanitizers, some manufacturers have introduced ozone sanitizers, which is known to be a potent sanitizer, for various surfaces as it is a highly reactive oxidizer. Ozone works well at killing various pathogens, and unlike chemical sanitizers, leaves no chemical residue on the treated surfaces. Ozone has been highly desirable for use in food processing plants, but otherwise has had limited practical applications. A sanitizing processing system using ozone is generally of limited use because the system must control the output of ozone in a sealed environment due to various potential health issues related to exposure to ozone. Therefore, ozone as a sanitizer is only used in large industrial settings and has not been successfully implemented in households or small commercial applications. More specifically, the application of ozone sanitizing systems has been extremely limited by the more recent understanding that ozone may cause various health issues, including according to the EPA, respiratory issues such as lung function, decrements, inflammation and permeability, susceptibility to infection, cardiac issues and increasing respiratory symptoms including increased medication use, asthma attacks and more. Exemplary respiratory symptoms from ozone exposure can include coughing, throat irritation, pain, burning, or discomfort in the chest when taking a deep breath, chest tightness, wheezing or shortness of breath. For some people, more acute or serious symptomatic responses may occur. As the concentration at which ozone effects are first observed depends mainly on the sensitivity of the individual, even some parts per billion exposure may cause noticeable issues. Therefore, other than commercial environments where the ozone application may be specifically controlled, these systems are not desirable for a broader implementation in homes, work places and other facilities, where the ozone is not easily contained, such as apparatuses that function as a door handle sanitizer for an operational door.

Therefore, there is a need for an effective sanitizer that does not include the above identified limitations.

SUMMARY OF THE INVENTION

The present invention is directed to a sanitizer for sanitizing various surfaces including hands, hardware, fixtures, appliances, countertops, equipment, utensils and more and more specifically to a chemical-free sanitizer, more specifically to an ozone-free sanitizer and yet more specifically to an electronic sanitizer and yet more specifically to an ion source sanitizer.

BRIEF DESCRIPTION OF THE DRAWINGS

Other advantages of the present invention will be readily appreciated, as the same becomes better understood by reference to the following detailed description when considered in connection with the accompanying drawings wherein.

BRIEF DESCRIPTION OF THE DRAWINGS

The present invention is generally directed to a sanitizer 10. The sanitizer 10 generally produces charged ions that are expelled by the sanitizer 10 toward an object or surface to be sanitized. The sanitizer 10 is specifically configured to avoid the production of ozone and should not be confused with ozone sanitizers. Instead, the present invention provides a compact ion sanitizer 10 that avoids the production of ozone and therefore sanitizes without ozone. Careful configuration of the ion sources 60 and voltage is required to avoid the production of ozone instead of ions.

Figure 1:
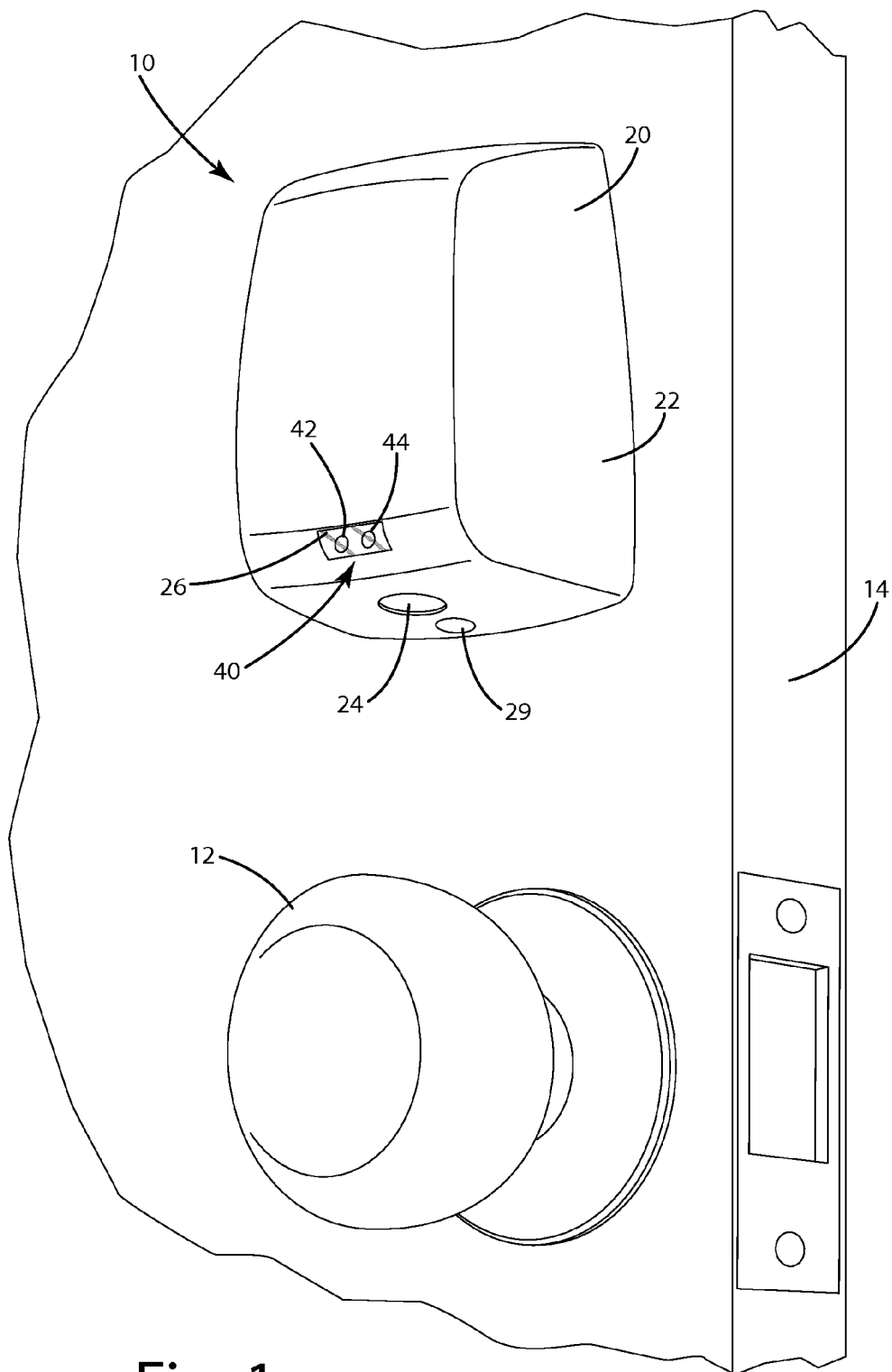
FIG. 1 is a front bottom perspective view of an exemplary sanitizer mounted on a door.
Figure 2:
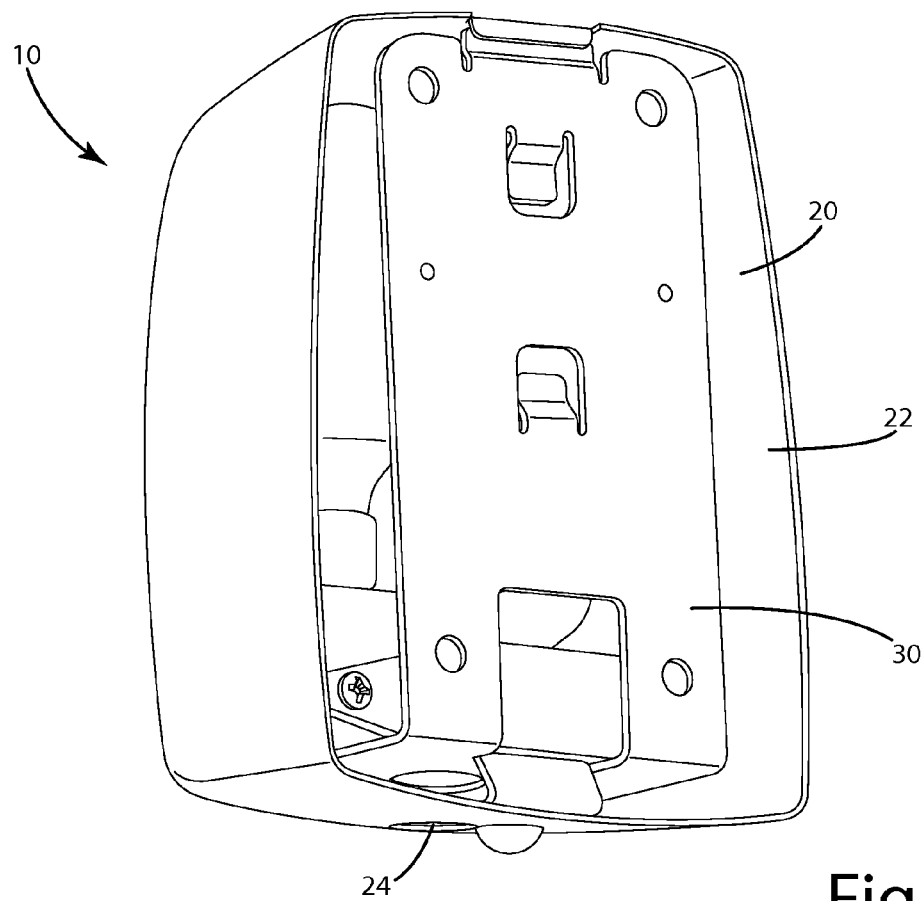
FIG. 2 is a rear perspective view of the exemplary sanitizer.

The sanitizer 10 generally includes an outer shell 20 which may further include a housing 22 and a backplate 30. The housing 22 is generally provided to protect the interior components of the sanitizer and to provide pleasing look and feel to the sanitizer. Of course, the housing 22 may be made in any size, shape, style, or configuration and in some embodiments where the sanitizer 10 itself is hidden or protected, the sanitizer 10 may be formed without a housing. The outer shell 20 further includes the backplate 30 which may also be configured in any size, shape or configuration. The backplate 30 is generally used to mount the sanitizer 10 to another surface such as a door, wall, fixture, or proximate to any other surface or fixture requiring sanitization. It is possible also to mount the sanitizer out of sight such as under a restroom sink with a tube extending out therefrom and ending proximate to the surface to be sanitized. Of course, in any such configuration the ion source 60 should be proximate to the end of the tube or to the exit of the sanitizer 10. As described below it has been found generally desirable to keep the source 60 of the ions as close as possible to the outlet passage 24 on the sanitizer and more preferably close to the surface to be sanitized. As illustrated in FIG. 1, the housing 22 is shown to generally include an outlet passage 24. While the sanitizer 10 may use timed disbursements, the sanitizer 10 illustrated in FIG. 1 uses motion activated disbursements. More specifically, the sanitizer 10 includes a housing 22 having a lens 26 which allows motion to be sensed by a motion sensor system 80, which initiates the process of sanitizing the surface. For example, if the sanitizer 10 is configured as a door handle sanitizer, the approach of a person toward the door handle may activate the sanitizer 10 such that a person knows the door handle has been sanitized. In the illustrated example, a puff of compressed gas may be heard by a user. Of course, a motion sensitive sanitizer 10 may also at timed intervals discharge ions to ensure that the desired surfaces stay sanitized.

Of course, the house illustrated in FIG. 1 may be formed without a lens. FIG. 1 also illustrates a portion of the housing fastening mechanism 28, specifically the screw 29. Of course, other fastening mechanisms located out of sight such as on the bottom to attach the housing 22 to the backplate 30 and thereby to a surface to which the backplate 30 is coupled may be used, such as snaps or any other method of fastening the housing 22 to the backplate 30.

Figure 3:
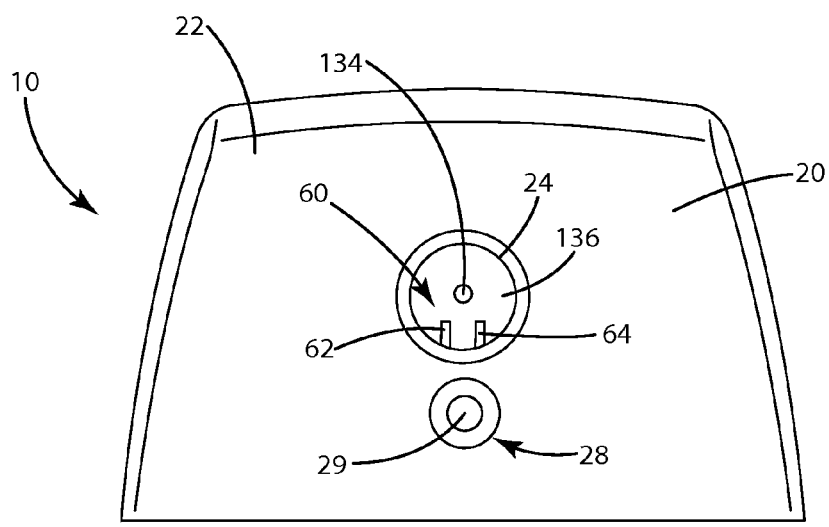
FIG. 3 is a bottom plan view of the sanitizer showing an anode and cathode of the ion sources.

As illustrated in FIG. 3, the sanitizer 40 is shown from a rear perspective view, illustrating the surface of the backplate 30 that is configured to mount to a supporting surface. While the backplate 30 only covers a portion of the perimeter of the housing 22, various sizes, shapes, styles, and configurations of the backplate may be used. The configuration of the backplate 30 may vary depending on what surface the backplate 30 is mounted. The backplate 30 illustrated in FIG. 3 only covers a portion of the housing 22 opening but may be configured to completely enclose the housing 22. As such, FIG. 3 also illustrates various working assemblies of the sanitizer including the power inverter 92 and controls 102 as well as compressed gas tanks 112 such as $CO_2$ tanks. The use of the compressed gas tanks 112 will be described in more detail below.

Figure 5:
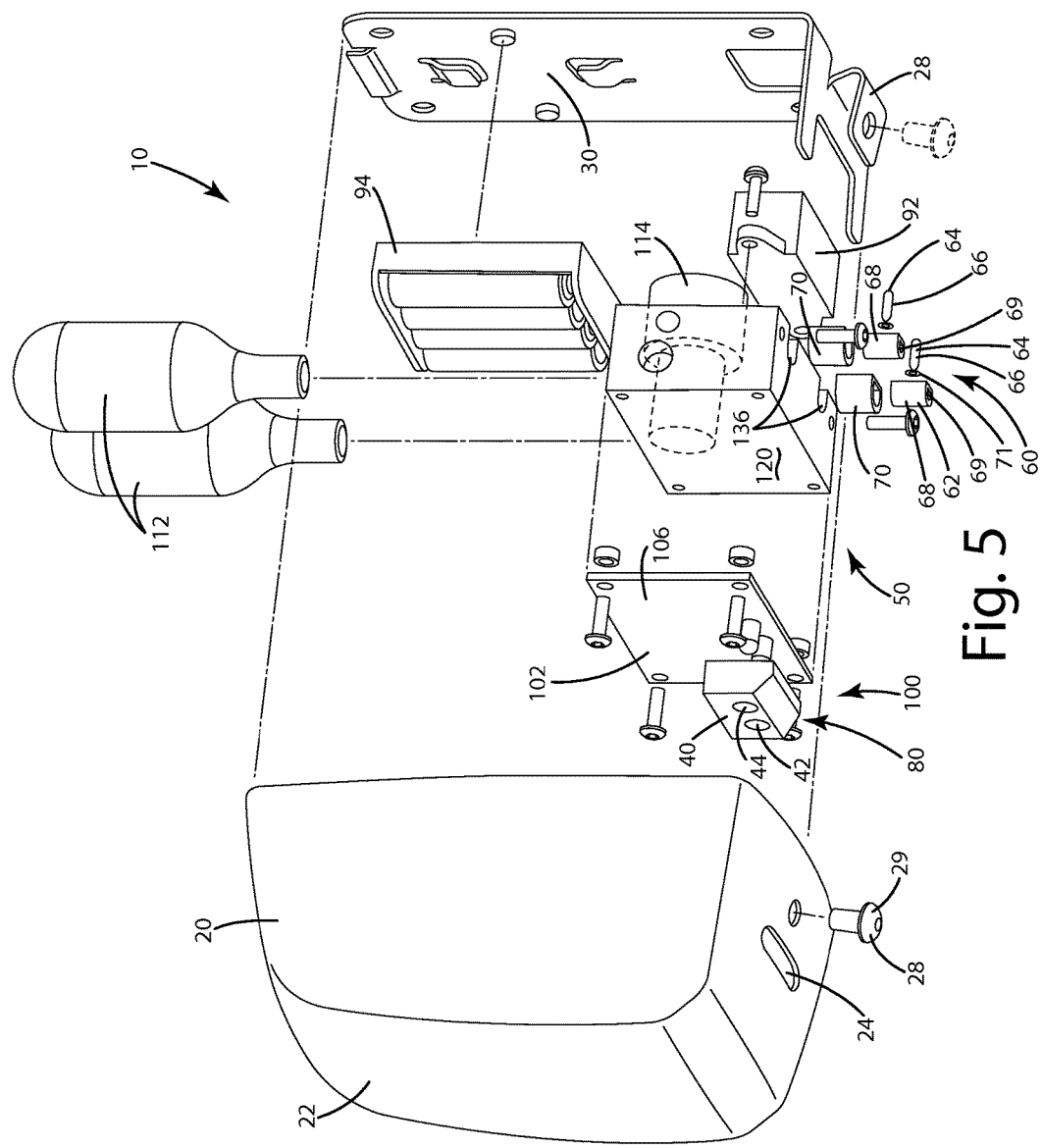
FIG. 5 is an exploded side perspective view of the sanitizer.

FIG. 5 illustrates the bottom of the sanitizer 10 including an outlet passage 24 defined by the housing 22. Of course, the outlet passage 24 may occur in other places on the housing 22, depending upon the desired application, size, shape, and style of the sanitizer 10. The location of the outlet passage 24 being on the bottom is only for convenience, however, it has been found helpful to have the exit on the bottom of the sanitizer 10 at times as $CO_2$ gas is generally heavier than the ambient air, helping disperse the ions downward using the available natural forces. FIG. 5 also illustrates the compressed gas exit 134 out of a manifold 120 and an ion source 60 arranged below the compressed gas exit 134, configured to have an anode 62 and cathode 64. Of course, the anode 62 and cathode 64 may have a variety of sizes, shapes, and some of such varied configurations are illustrated in the exemplary embodiments in the later drawings. It is generally desirable to have the anode 62 and cathode 64 within set distance of each other to ensure that production of ozone is minimized or eliminated. In the illustrated embodiment of FIG. 5, the anode 62 and cathode 64 stick into the space between the outlet passage 24 in line with the compressed gas exit 134, which forces the ions, produced by the ion source 60, particularly the anode 62 and cathode 64, to be pushed outwardly away from the sanitizer 10.

Figure 4:
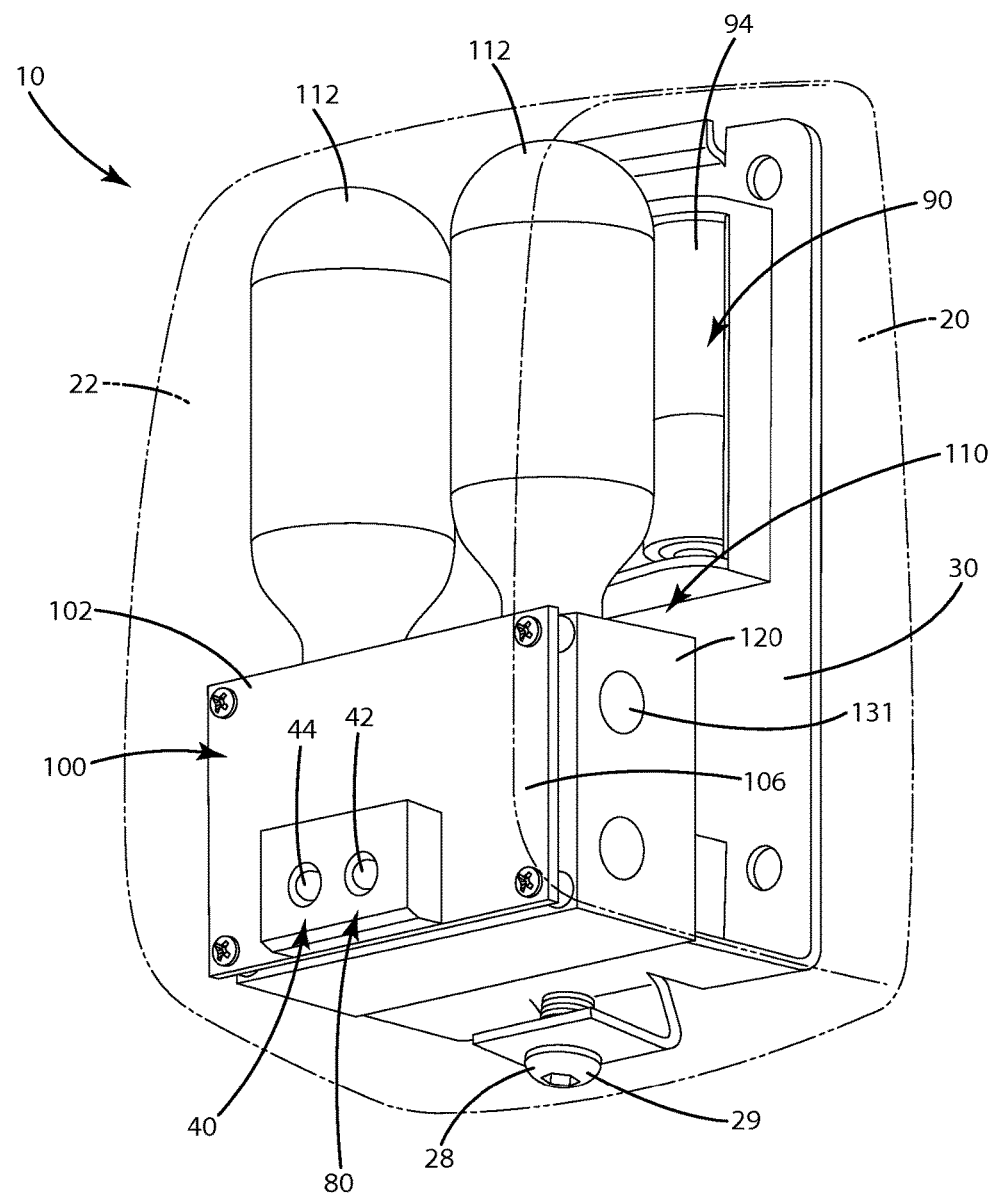
FIG. 4 is a front perspective view of the sanitizer without the housing.
Figure 6:
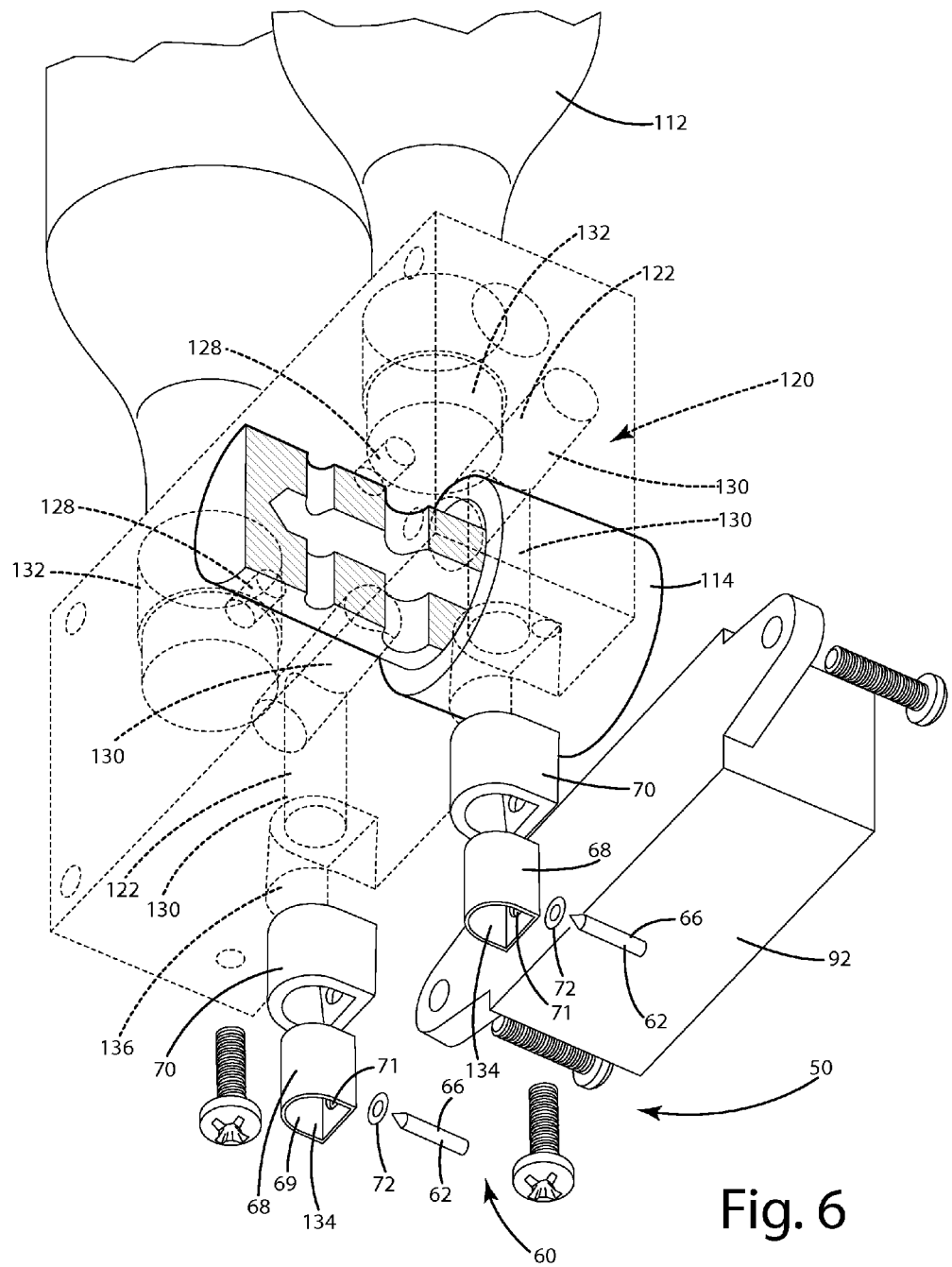
FIG. 6 is an enlarged bottom partial perspective view of the sanitizer including the manifold being shown partially transparent to illustrate internal passageways with the valve in a closed position.
Figure 7:
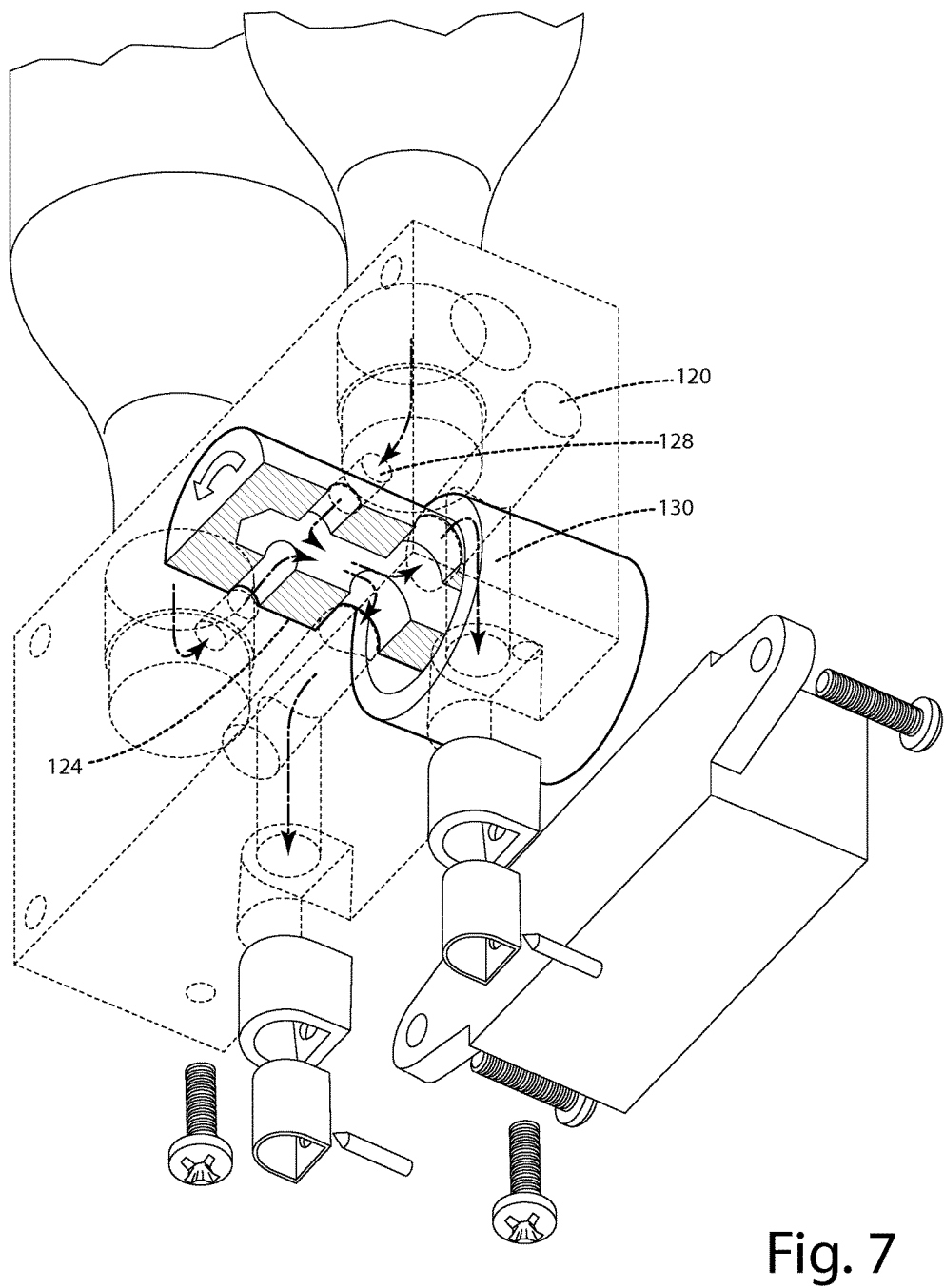
FIG. 7 is an enlarged bottom perspective view including the manifold being shown partially transparent to illustrate internal passageways with the valve in the open position and the compressed gas flows being illustrated.

FIG. 4 illustrates a sanitizer 10 with the housing removed. FIGS. 6 and 7 are provided such that the operational components as well as the passages for compressed gas to pass through the manifold may be easily visualized. As illustrated in FIGS. 4 and 5, the sanitizer includes the optional motion sensor or detector 40 such as the illustrated infrared sensor 42 and emitter 44. As discussed above, a motion sensor 40 may be used to activate the sanitizer to maximize the time interval before replacement of the gas cylinders 112 or power battery pack 94 is required. The motion sensor or detector 40 may be part of the control system 100 and sit on a circuit board 106 having controls 102 for the activation of the other componentry as well as communicating with the detector 40. The circuit board 106 generally forms the electronics and controls 102 necessary to activate the sanitizer 10. Of course, although not illustrated, these control functions may be separated into discrete electronic components. Any type of motion sensor or sensor block may be used as the detector 40. A timer may be used in addition to or in place of the motion sensor and detector 40 block to sanitize the fixture at specified intervals with the sanitizer 40.

As illustrated in the Figures, the sanitizer 10 may use compressed gas cylinders 112 inserted into a manifold 120. The sanitizer 10 may include a single cylinder 112 or multiple cylinders, such as the two cylinders 112 illustrated. The number of cylinders 112 is generally a balance between providing more cylinders of compressed gas to minimize maintenance intervals for the required replacement of the gas cylinders and the size of the sanitizer 10. Of course, as more cylinders 112 are added, the size requirements increase thereby limiting its applicable to many desirable surfaces, such as acting as a door handle sanitizer. Of course, under counter sanitizers or sanitizers that are placed in areas where a larger footprint is acceptable may use larger cylinders, more cylinders, or even rechargeable cylinders. For example, in certain commercial applications, large $CO_2$ tanks, similar to that used to carbonate beverages may be used. In some facilities where a gas source is readily available, the cylinders may be eliminated and a gas supply is piped directly to the manifold. The compressed gas cylinders 112 are expected to be $CO_2$ gas although any other compressed gas that is safe for use around humans may be used. Another reason for the use of $CO_2$ gas cylinders is that it has been found that $CO_2$ is very effective at propelling the ions away from the ion source to the surface to be sanitized, as compared to other gases such as nitrogen ($N_2$) or even compressed air. It also has been found that the ions from one of the anode and cathode are expelled nicely away from the sanitizer with minimum breakdown or disappearance of the ions within the compressed gas, particularly with use of $CO_2$ as the compressed gas.

While FIGS. 4 and 5 show a perspective view of the sanitizer 10 with the control system 100 including electronic controls 102 and detector 40 for activating the sanitizer manifold block 120 into which the gas cylinders 112 are secured and the power assembly 90, FIGS. 6 and 7 illustrate the variety of passages 122 that route the compressed air from the gas cylinders 112 through a solenoid or other valve 114 that releases desired amounts of gas to propel the ions away from the exit 134 and outlet passage 24. The amount of gas released is carefully balanced to ensure that the ions are sufficiently dispersed while in the air or gas stream toward the desired surface, minimizing the expelled gas to minimize the replacement of tanks 112 after installation of the sanitizer. Maintenance of the sanitizer 10 also generally includes replacing of the battery 94, replacing of the gas cylinders 112 and any repair work. Regular maintenance not considered repair work would be replacing of the batteries 94 and replacing of the gas cylinders 112. Of course, it is desirable to minimize any maintenance. The manifold 120 may be made in any desired size, shape, style, or configuration so long as it is capable of routing in a compact fashion the gas from the compressed gas cylinders 112 through the manifold 120 to the outlet passage 24 and expel the ions from the ion source 60 to the desired surface. As illustrated in FIGS. 6 and 7, the manifold block is shown with the passages 122 visible as well as how the gas cylinders 112 are inserted into the manifold 120. As illustrated in FIGS. 6 and 7, a valve, such as a two-way solenoid pneumatic valve I sued, which allows metering of the compressed gas. As stated above, it is desirable to provide the minimum amount of gas necessary to expel the ions sufficiently from the sanitizer 10 to reduce the number of times that the compressed gas cylinders 112 need to be replaced. The present invention found a balance of sanitizing the surfaces or objects within 12 inches in less than 3 seconds, while maximizing time periods between required maintenance.

As illustrated in FIGS. 6 and 7, the manifold 120 may include a valve cavity 124 and a solenoid cavity 126 with inlet passages 128 from the compressed gas supply that extends thereto and outlet passages that extend therefrom to the exit 134.

FIGS. 4 and 5 illustrate the power supply assembly 90, which is specifically illustrated as a battery pack 94 but of course, where available, the sanitizer 40 may be configured to use a normal electrical outlet or a hardwire option as a power input. In most instances, it is expected that the sanitizer 10 will be spaced from or not capable of being powered from a wall outlet or a facility's electrical system and therefore, a battery pack 94 is provided in the illustrated examples. The battery packs 94 are expected to use either rechargeable batteries or replaceable standard sized batteries, each which will be typically replaced or recharged when the gas cylinder is replaced or recharged. It has been surprisingly found that the sanitizer, which does not produce ozone, may be configured to produce sufficient ions to sanitize a nearby surface as well as operate a solenoid to meter the amount of released air or compressed gas. The illustrated power supply is configured to use AA batteries, such as standard or rechargeable AA batteries. To improve longevity, items like photo cell batteries that are configured for long life may be used in place of standard batteries. Of course, the power supply may have any desired size, shape, style, or configuration so long as it is capable of supplying the necessary power over time as well as being easily replaceable or rechargeable by office workers, cleaning staff, and the like.

FIG. 5 provides an exploded perspective view of an exemplary sanitizer 10 incorporating the present invention. One or more air or compressed cylinders 112 may be provided as well as a power supply 90, a sensor assembly 40, an electronics and control system 100, a housing 22, a backplate 30, and the operational ion mechanism 50 as well as the required inverter 96 and high voltage supply 98. The ion mechanism 50 generally includes the manifold 120 and an ion source 60 having an anode 62 and a cathode 64. As stated above, the manifold 120 in conjunction with the solenoid and the valve 114 is configured to release or define or desired amounts of compressed gas through passageways and then outwardly past or through the ion sources to eject or displace the ions away from the anode 62 and cathode 64. The ions upon reaching the surface sanitize the surface from various pathogens. As illustrated in FIG. 5, the manifold 120 which is generally formed out of a block of material, such as an aluminum block which is electrically conductive, may in certain configurations need to be insulted from the ion sources. It should be noted that the ion sources 60 in FIG. 3 are illustrated both as protrusions 66 while the ion sources 60 in FIG. 5 are a tube 68 and a protrusion 66. To isolate the tube 68 ion sources 60 from the manifold 120, an insulator 70 as illustrated in FIGS. 5-7 may be provided. Of course, the insulator 70 may take on a variety of sizes, shapes, and configurations so long as it presents electrical shorting of the ion sources 60. Of course, if the manifold 120 is not electrically conductive, the insulator 70 may be eliminated. As illustrated in FIGS. 5-7, at least half of the ion source 60, such as the anode 62, may be actually one of the walls surrounding the outlet passage, the illustrated tubes 68, through which the compressed gas passes. While gas exiting the manifold 120 may no longer be compressed, for ease of description, the term compressed gas is used. Inserted into this defined cavity of either the anode or cathode where the compressed gas is passed through may be the opposite, anode or cathode, such as the illustrated pins. For example, if the tube 68 is an anode 62, the protrusion 66 could be the cathode 64 of course they could be reversed. Of course, a variety of other anodes and cathodes, such as different sizes and configurations, may be used so long as they minimize or preferably eliminate the production of ozone and provide sufficient amount of ions when desired. The insulators 70 are provided to prevent the ion sources from short-circuiting out from the manifold 120 or when one of the anode 62 and cathode 64 are inserted through the other of the anode 62 and cathode 64. The ion sources 60 are controlled by the inverter 96 and high voltage supply 98, as illustrated. As illustrated in FIGS. 6 and 7, the supply or inlet passage 128 from the gas supply cavity 132 into the valve cavity 124 is visible as well as the output passages 130 from the valve cavity 124 extending to the exit passage 134 and the exit passage as it extends to the ion source cavity 136. Of course, the illustrated embodiment is exemplary and other routing systems and configurations of passages 122 may be used. The insulators 70 may be clearly seen as well the ion source 60 and the anodes 62 and/or cathodes 64. The power supply 90 may also be seen directly above the manifold 120.

As further illustrated in FIGS. 6 and 7, a plug 131 is supplied in part of the outlet passage 130 to allow for easy routing of the passages within the manifold block 120 during formation of the manifold 120. More specifically, the manifold 120 is cross drilled both for the outlet passage 130 and supply or inlet passages 138 through the valve cavity 124 and a plug 131 is provided on one end to prevent escaping of gases other than as directed across the ion sources 60. The Figures also illustrate the insulator 70 which may be seen to provide a hole 71 for the cathode. The anode 62 or cathode, typically anode, when formed as a rounded shell or tube 68 generally includes an ion insulator 72 to insulate the cathode 64 from the anode 62. The other main insulator 70 such as a manifold insulator helps insulate the anode 62 and cathode 64 from the manifold 120. It is not desirable for the anode 62 and cathode 64 to touch, and the manifold insulator 70 and ion insulator 72 prevent short-circuiting of the anode 62 and cathode 64 which would prevent the formation of ions. The ion insulator 72 also allows for easy assembly and controlled spacing of the anode 62 and cathode 64 to maximize the efficiency of the sanitizer 10 in producing ions while minimizing or eliminating any production of ozone.

Figure 8:
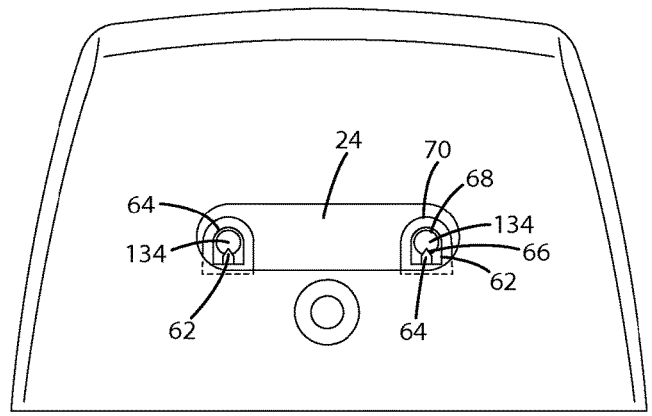
FIG. 8 is a bottom plan view of the sanitizer in FIG. 6.

As illustrated in FIG. 8, the housing may be formed in a different shape having a larger outlet passage 24. The double ion sources are spread away from each other requiring the larger outlet passage 24 on the housing 22. Of course, the system illustrated in FIGS. 5-8 may be easily configured to have a single ion source 60 instead of the dual ion sources illustrated. In some embodiments, of course, additional ion sources could be added.

Figure 9:
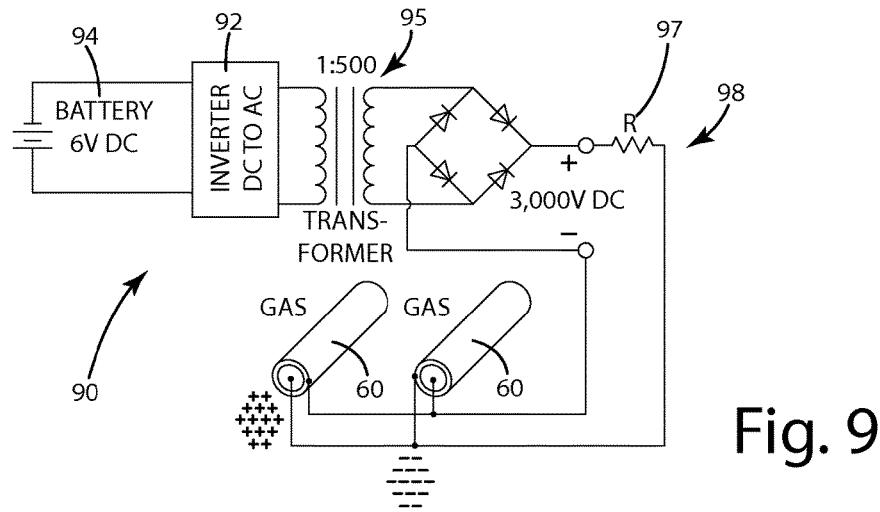
FIG. 9 is an exemplary schematic view of the electronics and power source being coupled to the ion sources with a transformer.
Figure 10:
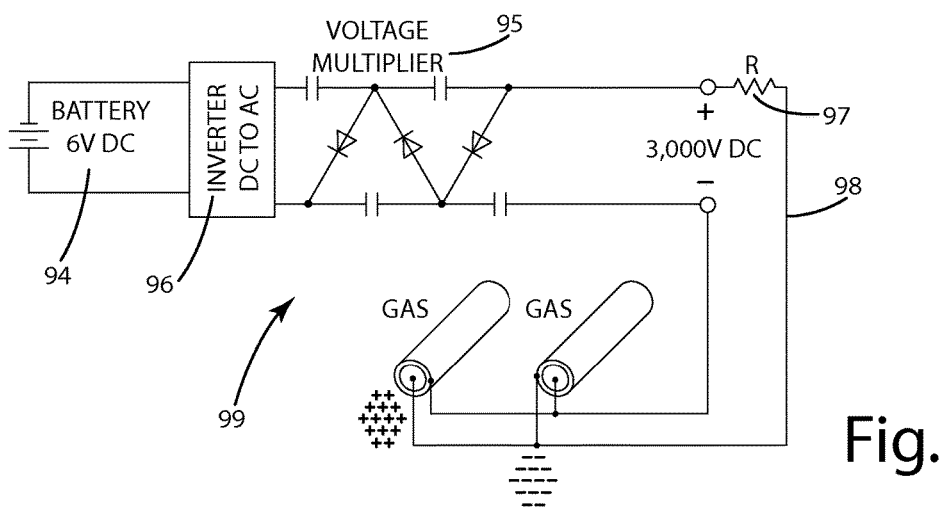
FIG. 10 is an exemplary schematic view of the electronics and power source being coupled to the ion sources with a voltage multiplier.

FIG. 9 illustrates a schematic diagram of the sanitizer 10 including the power assembly 9 specifically the batter pack 94 providing input into the inverter 96 which converts the DC from the battery to AC. While the battery pack is shown as a six volt DC battery pack, the battery pack may be formed from any other type of voltage and amperage input into the inverter. In fact, a higher voltage battery such as when used with the voltage multiplier illustrated in FIG. 10 may be beneficial. The inverter 96 transfers the DC power to AC which is the provided to a transformer. The transformer may be any type of transform although the illustrated transformer is a 1:500 transformer. From the transformer, the system passes the power to a high voltage supply 98 which includes a full wave rectifier 99. The high voltage power supply may also include a current resistor 97. Electrical lines pass the power to the ion sources 60 which are illustrated as the tube 68 and the protrusion or point 66. Either one of the tubes 68 and protrusions 66 may act as the anode 62 or cathode 64. FIG. 33 illustrates a similar schematic diagram, however, the transformer is replaced with a voltage multiplier 95.

Figure 11:
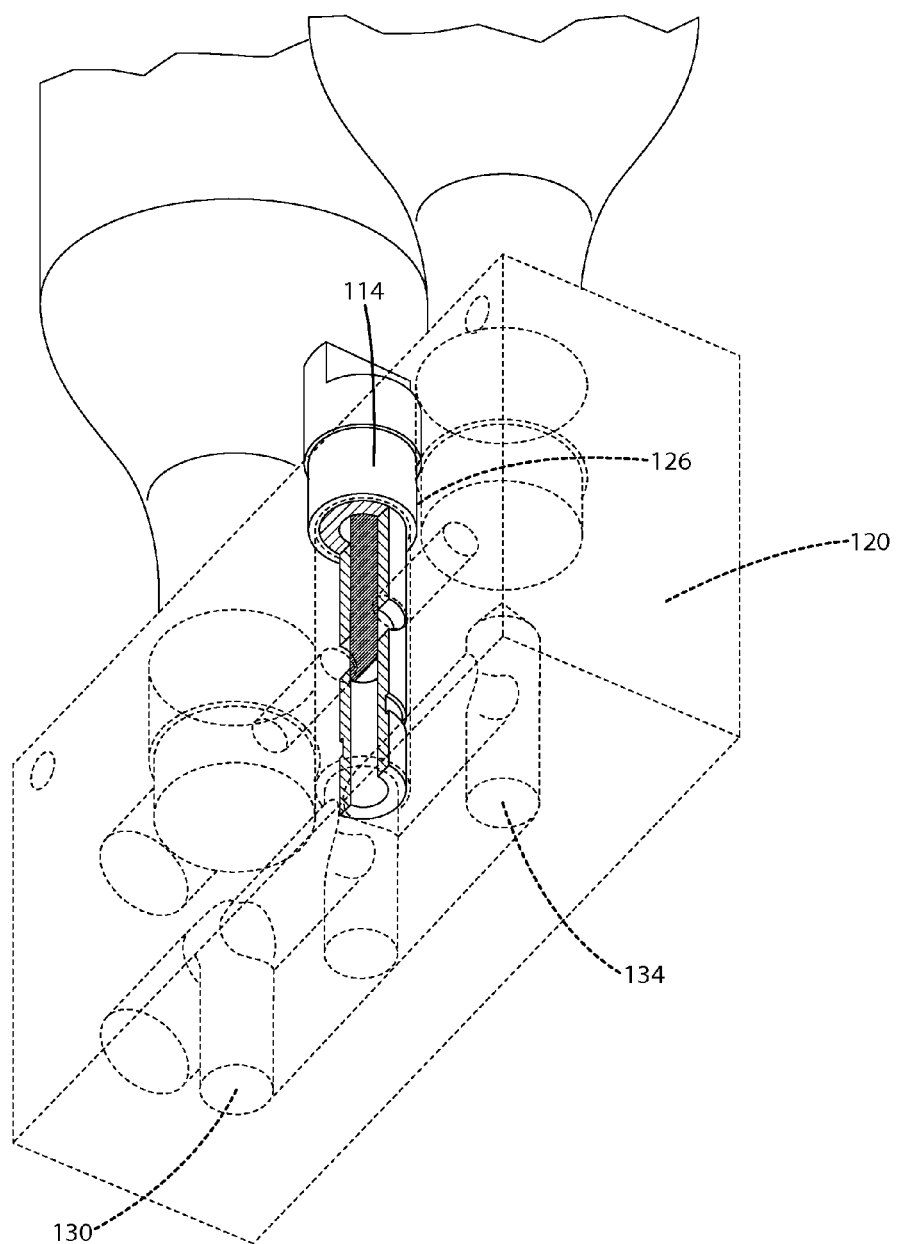
FIG. 11 is a bottom perspective view of a manifold being shown partially transparent to illustrate the internal passages and the solenoid being in a closed position.
Figure 12:
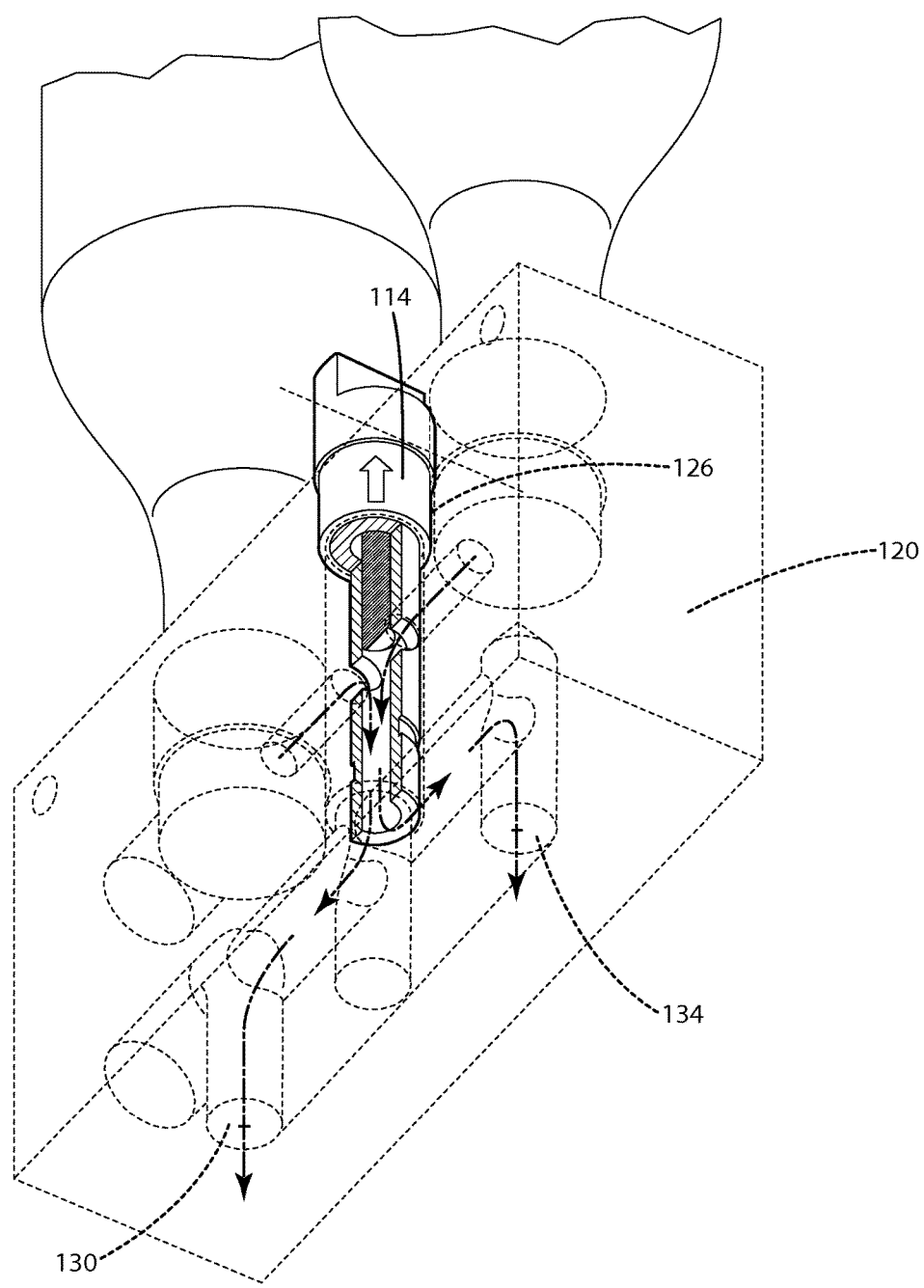
FIG. 12 is a front elevational view of the manifold being shown partially transparent to illustrate the internal passages and the solenoid being in an open position with the fluid flow of the compressed gas being illustrated.

FIGS. 11 and 12 illustrate a solenoid 114 in place of the valve and inserted into the solenoid cavity 126. The manifold 120 is manufactured in a similar fashion with similar passage 122, however, the passages 122 are slightly different due to the different operation of a solenoid in place of the rotary valve 114. From the gas cylinders 112, which are inserted into the gas supply cavity 132, the gas travels through the inlet passages 128 to the solenoid cavity 126. The solenoid 114 then controls the passage of the gas through the solenoid cavity 126 to the outlet passages 130. Gas then exits at 134 past the ion sources 60. FIG. 11 shows the solenoid in a closed position preventing the flow of the gas from the gas cylinders 112 while FIG. 12 shows the solenoid 114 in the open position allowing passage from the compressed gas tanks 112 to the exit 134. FIG. 12 also shows the fluid flow as the gas passes through the manifold 120.

Figure 13:
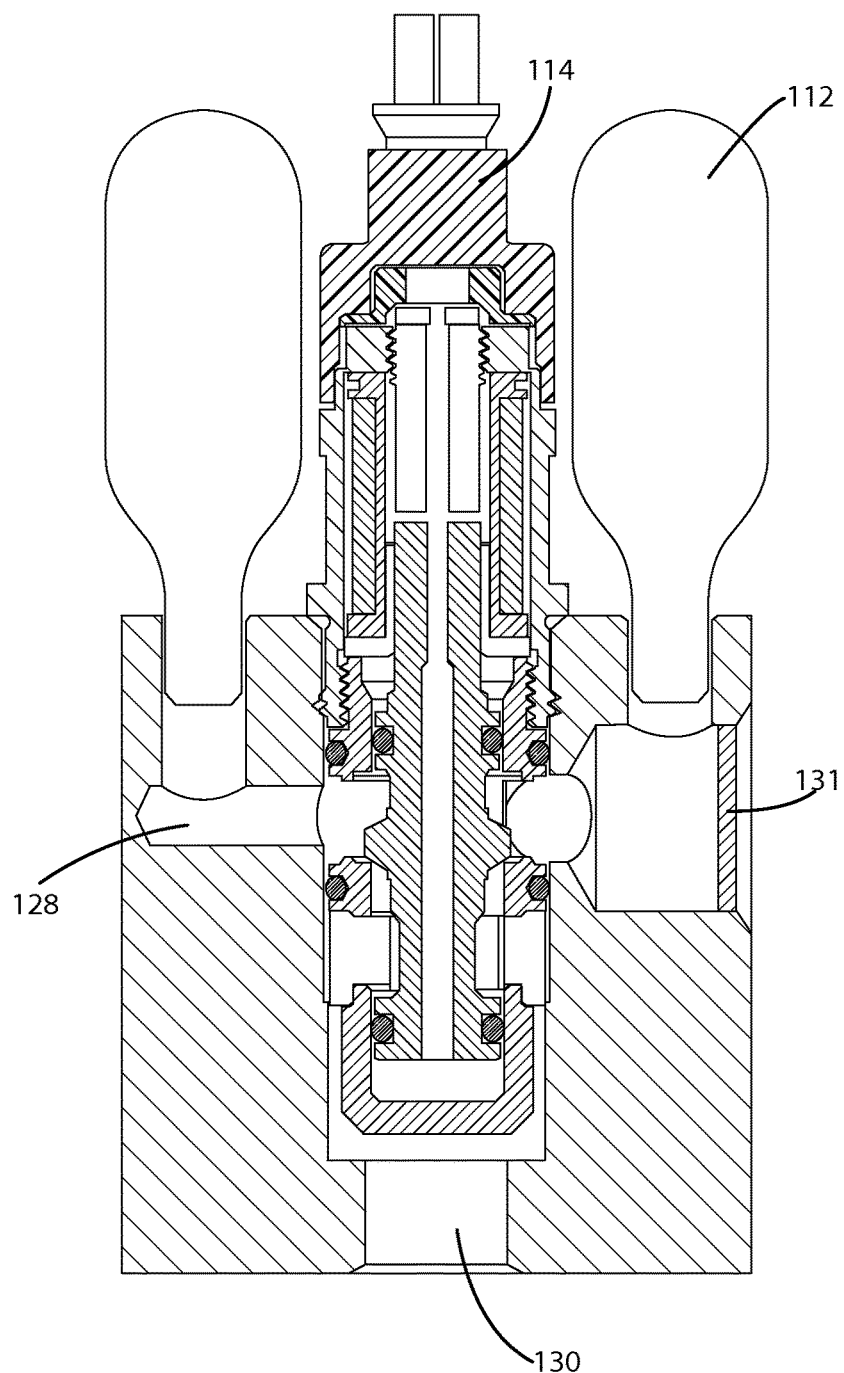
FIG. 13 is a front elevational view of a manifold and a solenoid of an exemplary sanitizer with the manifold being partially transparent to illustrate passageways.
Figure 14:
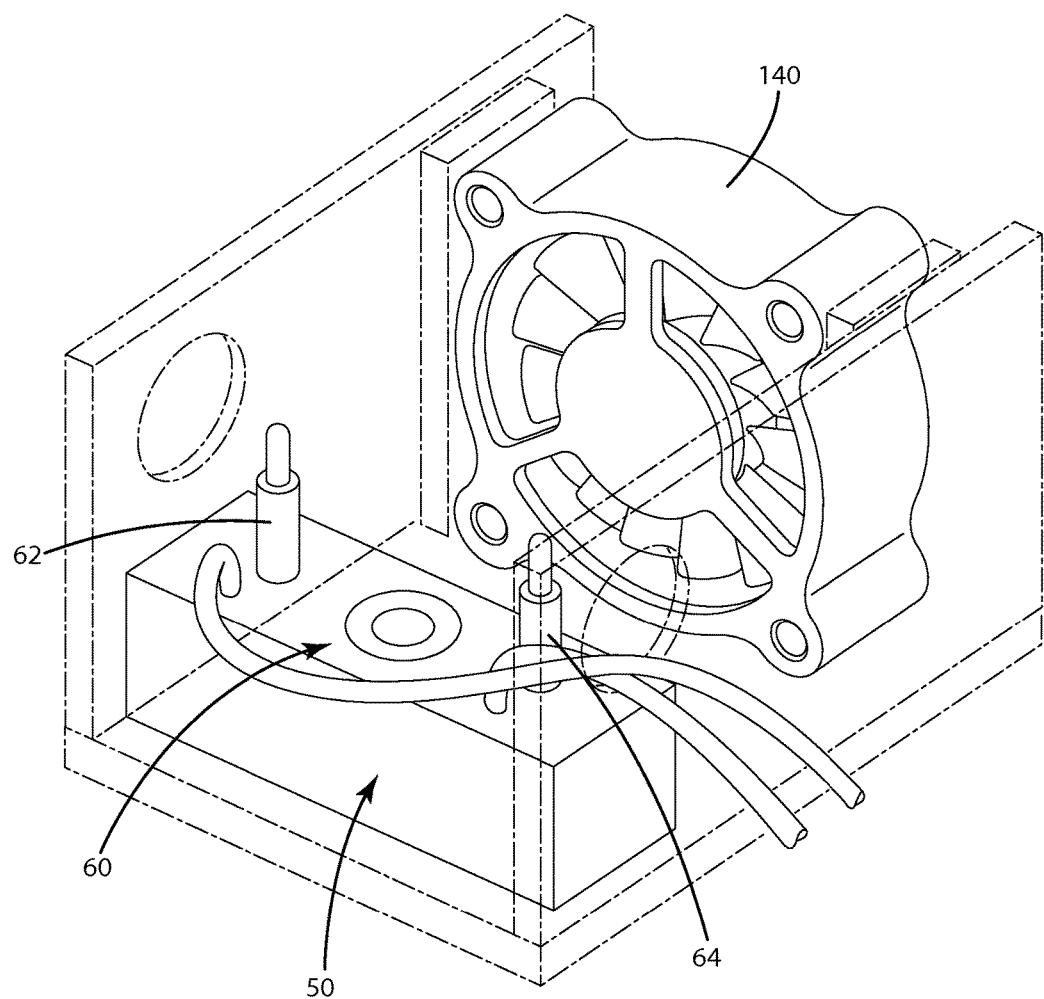
FIG. 14 is a perspective view of a sanitizer using a fan as an air source.

FIGS. 13 and 14 illustrate slight variations in the passages 122 and the manifold 120. However, the operation is very similar to the other manifolds 120 described above. Of course, the manifold 120 and passageways 122 may be configured in a variety of different sizes, shapes, and configurations to allow to fit different solenoid 114, gas cylinders 112, gas supplies and ion sources 60.

During operation, the sanitizer 10 supplies power from the power supply 90 to the inverter 96 which converts DC to AC power. Of course, if AC power is readily available such as from a wall outlet, the power supply 90 would not be needed nor would the inverter 96 be needed. The inverter converts the DC to AC power which is then provided to a voltage step up apparatus. As illustrated in the Figures, the step up apparatus may have a variety of configurations, however, it has been generally found to have a voltage output of 1,000 to 5,000 DC, preferably 2,000 to 4,500, preferably 2,500 to 3,500 and more preferably 3,000 volts DC to provide the ion sources with sufficient power to generate ions yet prevent the creation of ozone. The spacing of the anode from the cathode is approximately 3 to 6 mm to prevent the generation of ozone, of course depending on the voltage applied, this distance can vary to prevent generation of ozone.

Therefore, during operation the control system 100 through either a motion sensor 80 or a timed device determines that the sanitizer needs to operate. The controls 102 on the circuit board 106 provide a signal to allow power to pass from the battery pack 94 through the inverter 96 and high voltage supply 98 to the ion sources 60. At the same time, the controls 102 would operate the solenoid or valve 114 which allows compressed gas in the compressed gas tank 112 of the propulsion mechanism 110 to pass through the manifold 120 using the passages 122. As the solenoid opens and closes, it can be configured to measure a precise amount of compressed gas that allows the ions to be ejected away from the ion sources 60 toward the desired surface while yet minimizing the amount of gas used to reduce how often the compressed gas tanks 112 need to be replaced. More specifically, the compressed gas travels through the passages 122 and the manifold 120 from the gas supply cavity 132 through the inlet passages 128 to either a valve cavity 124 or solenoid cavity 126. In a closed position, the compressed gas is at pressure in the inlet passages 128. When the solenoid 114 or valve open, the compressed gas passes through the outlet passages 130 toward the exit 134. In doing so, they will pass through the ion source cavity 136, pass the ion sources 60 moving the positive and negative ions from the anode and cathode 62, 64. As illustrated in the Figures, the manifold when formed may include a variety of plugs 131 which allows straight drilling of the various passages 132. Of course, the manifold 120 may be formed from other materials such as a molded plastic or non-conductive material. In some embodiments, the manifold 120 may act as one of the anode or cathode 62, 64 with an additional point or protrusion 66 aligned with the ion source cavity 136. In such an embodiment, the insulators 70 and 72 would not be required. However, in some circumstances, the ion insulator 72 may be required to insulate the protrusion 66 of either the anode or cathode 62, 64 from the manifold 120 which is acting as one of the ion sources 60.

The sanitizer can also count the number of cycles and when it approaches a predetermined number of cycles provide some form indication to the user or facility manager that replacement of battery of gas cylinders is needed, preferably before either one is exhausted.

Obviously, many modifications and variations of the present invention are possible in light of the above teachings and may be practiced otherwise than as specifically described while within the scope of the appended claims. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims. In addition, the reference numerals in the claims are merely for convenience and are not to be read in any way as limiting.

What is claimed is:

1. A sanitizer comprising:
   an ion system, including at least two ion sources capable of generating ions;
   a gas supply;
   a manifold having passages and an exit and wherein said at least one ion source is located proximate to said exit, said manifold being configured to direct gas from said gas supply to said exit; and
   including at least one of an anode and at least one of a cathode; and
   wherein said at least one ion source includes a tube configured to fit within said ion source cavity; and
   wherein said tube acts as one of said at least one anode and at least one cathode;
   a propulsion mechanism capable of displacing the ions away from said ion source;
   wherein said propulsion system further includes a valve dividing said passages between inlet passages and outlet passages and wherein said inlet passages extend between said gas supply and said valve and wherein said outlet passages extend between said exit and said valve.

2. The sanitizer of claim 1 wherein said gas supply is selected from one of a gas inlet and at least one compressed gas tank.

3. The sanitizer of claim 1 wherein said gas supply is at least one compressed gas tank directly coupled to said manifold.

4. The sanitizer of claim 1 wherein said valve is located in a valve cavity and selected from one of a rotary valve and solenoid valve.

5. The sanitizer of claimer 1 wherein said outlet passages proximate to said exit form an ion source cavity and wherein said ion source cavity is configured to receive said ion sources.

6. The sanitizer of claim 1 wherein said tube includes a tube cavity and said at least one ion source includes a protrusion extending at least partially into said tube cavity.

7. The sanitizer of claim 6 wherein said protrusion is at least one of said at least one anode and said at least one ion cathode and wherein said tube and said protrusion extending into said tube cavity are opposing selections of said at least one anode and said at least one cathode.

8. The sanitizer of claim 6 wherein said tube defines a hole configured to receive an ion insulator and wherein said ion insulator insulates said protrusion from said tube.

9. The sanitizer of claim 1 further including a manifold insulator located between said tube and said manifold.

10. The sanitizer of claim 1 further including a motion sensor system.

11. The sanitizer of claim 1 wherein said ion system includes at least one anode and at least one cathode forming said at least one ion source, a power assembly; and a control system.

12. The sanitizer of claim 11 wherein said power assembly includes a power inerter, a battery pack, a voltage multiplier, and a full wave rectifier.

* * * * *